US006807842B2

(12) United States Patent
Williams et al.

(10) Patent No.: US 6,807,842 B2
(45) Date of Patent: Oct. 26, 2004

(54) MOLECULAR RECOGNITION SENSOR SYSTEM

(75) Inventors: John R. Williams, Lexington, MA (US); Christopher E. Dubé, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 308 days.

(21) Appl. No.: 09/954,655

(22) Filed: Sep. 18, 2001

(65) Prior Publication Data

US 2003/0053935 A1 Mar. 20, 2003

(51) Int. Cl.$^7$ .............................................. G01N 27/04
(52) U.S. Cl. .................. 73/23.2; 73/31.05; 338/34; 422/82.02; 422/98
(58) Field of Search ........................... 73/23.2, 31.05; 338/34; 422/82.02, 98

(56) References Cited

U.S. PATENT DOCUMENTS

| | | | | |
|---|---|---|---|---|
| 5,007,283 A | * | 4/1991 | Ambos | 73/1.07 |
| 5,571,401 A | | 11/1996 | Lewis et al. | |
| 5,698,089 A | | 12/1997 | Lewis et al. | |
| 5,788,833 A | | 8/1998 | Lewis et al. | |
| 5,891,398 A | | 4/1999 | Lewis et al. | |
| 5,911,872 A | | 6/1999 | Lewis et al. | |
| 5,951,846 A | | 9/1999 | Lewis et al. | |
| 5,959,191 A | | 9/1999 | Lewis et al. | |
| 6,010,616 A | | 1/2000 | Lewis et al. | |
| 6,232,783 B1 | * | 5/2001 | Merrill | 73/19.1 |
| 6,458,327 B1 | * | 10/2002 | Vossmeyer | 422/98 |
| 2002/0045275 A1 | * | 4/2002 | Huang | 436/518 |
| 2002/0102312 A1 | * | 8/2002 | Tepper et al. | 424/490 |

FOREIGN PATENT DOCUMENTS

EP           609316 B1  *  10/1994

OTHER PUBLICATIONS

Piletsky et al. "Imprinted Membranes for Sensor Technology: Opposite Behavior of Covalently and Noncovalently Imprinted Membranes" Macromolecules Mar. 1998, vol. 31, pp. 2137–2140.*

Nesim Sallacan et al., *Imprinting of Nucleotide and Monosaccharide Recognition Sites in Acrylamidephenylboronic Acid—Acrylamide Copolymer Membranes Associated with Electronic Transducers*, 74(3) Analytical Chemistry 702 (2002), no month.

Jenkens et al., "Polymer–Based Lanthanide Luminescent Sensor for Detection of the Hydrolysis Product of the Nerve Agent Soman in Water" 71 Anal. Chem. 373–378 (1999).

Arnold et al., "Progress in the Develpment of Molecularly Imprinted Polymer Sensors" 20 Johns Hopkins APL Technical Digest, No. 2, pp. 190–198 (1999).

Takeuchi et al., "Combinatorial Molecular Imprinting: An Approach to Synthetic Polymer Receptors" 71 Anal. Chem. No. 2, pp. 285–290 (1999).

(List continued on next page.)

Primary Examiner—Michael Cygan
(74) Attorney, Agent, or Firm—Iandiorio & Teska

(57) ABSTRACT

A molecular recognition sensor system for detecting the presence and concentration of an analyte including a resistive sensor having a semiconductive polymer film which swells when exposed to an analyte and interferents and a molecular imprinted resistive sensor having a semiconductive polymer film imprinted with the analyte which thereby swells when exposed to interferents, a circuit connected to the resistive sensor and the molecular imprinted resistive sensor for detecting a change in the resistance of the resistive sensor when exposed to the analyte and the interferents, the change in the resistance of the molecular imprinted resistive sensor when exposed to the analyte and interferents, and for subtracting the change in resistance of the molecular imprinted resistive sensor from the change in resistance of the resistive sensor to reduce the effect of any interferents on the change in resistance of the resistive sensor thereby determining the presence and concentration of the analyte.

17 Claims, 8 Drawing Sheets

OTHER PUBLICATIONS

Ramstrom et al., "Applications of Molecularly Imprinted Materials as selective Adsorbents: Emphasis on Enzymatic Equilibrium Shifting and Library Screening" 47 Chromatographia No. 7/8, pp. 465–469 (Apr. 1998).

Ramstrom et al., "Screening of a Combinatorial Steroid Library Using Molecularly Imprinted Polymers" 35 Anal. Commun. 9–11 (Jan. 1998).

Mirsky et al., "A Spreader–Bar Approach to Molecular Architecture: Formation of Stable Artificial Chemoreceptors" 38 Angew. Chem. Int. Ed, No. 8, pp. 1108–1110 (1999).

Sabourin et al., "Molecularly Imprinted Polymer Combinatorial Libraries for Multiple Simultaneous Chiral Separations" 35 Anal. Commun. 285–287 (1998).

Borje Sellergren, "Imprinted Polymers with Memory for Small Molecules, Proteins, or Crystals" Angew. Chem. Int. Ed. No. 6, pp. 1031–1037 (2000).

Yilmaz et al. "The Use of Immobilized Templates—A New Approach in Molecular Imprinting" Angew. Chem. Int. Ed. No. 12, pp. 2115–2118 (2000).

* cited by examiner

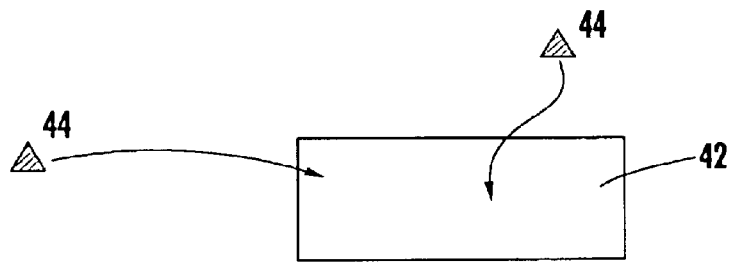
FIG. 3A.
(PRIOR ART)
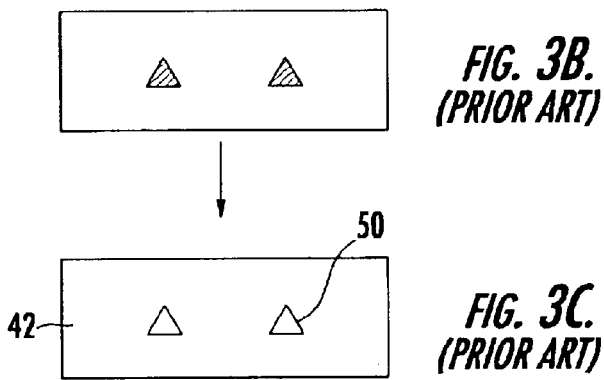
FIG. 3B.
(PRIOR ART)
FIG. 3C.
(PRIOR ART)
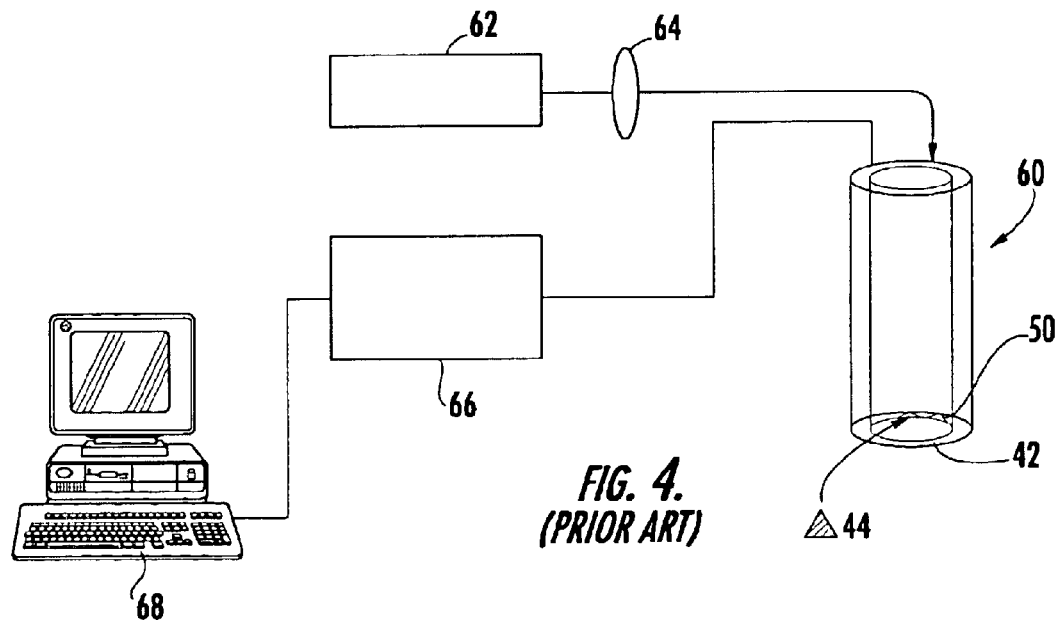
FIG. 4.
(PRIOR ART)

MOLECULAR RECOGNITION SENSOR SYSTEM

FIELD OF THE INVENTION

This invention relates to a molecular recognition sensor system for detecting the presence and concentration of an analyte and to a method of detecting the presence and concentration of an analyte.

BACKGROUND OF THE INVENTION

Numerous methods exist for the chemical detection of analytes. For example, resistive sensors measure the change in resistance when an analyte and interferents are absorbed by the semiconductive polymer film on the sensor. The absorption of the analyte and interferents cause the semiconductive polymer film to swell which changes the resistive properties of the sensor.

However, these devices are non-specific to an analyte because they cannot distinguish between the absorption of the analyte and the absorption of the interferents in the polymer film of the sensor. Because both the analyte and the interferent will cause a device to swell and correspondingly affect the resistance, to be selective to the analyte these prior art resistive sensors must rely on an array of chemical coatings on the sensor and on pattern recognition. See U.S. Pat. Nos. 5,571,401, 5,698,089, 5,788,833, 5,891,398, 5,911,872, 5,951,846, 5,959,191, and 6,010,616 to Lewis et al. incorporated herein by this reference. These prior art resistive sensors are non selective and require extensive data manipulation. Further, the chemical coatings on the resistive sensor will absorb virtually any interferents which will impair the ability of the sensor to detect the change in resistance due to the analyte.

Other prior art techniques attempt to detect an analyte by molecularly imprinting a polymer. These techniques employ a polymer film to which an analyte of interest is added, the polymer cured, then the analyte is removed by washing. The result is a polymer with cavities the same size as the analyte. The polymer is typically applied to a fiber-optic sensor to which luminescence is applied via an argon ion laser with a holographic filter, and results analyzed on a computer. Other variations to detect the analyte in the imprinted polymer include measurement of the UV, infrared, and visible light absorption as well as fluorescence and phosphorescence. See e.g. *Polymer-Based Lanthanide Luminescent Sensor For Detection Of The Hydrolisis Product Of The Nerve Agent Soman In Water*, Jenkens et al., Anal. Chem. Vol. 71, p.373–378 (1999) and *Progress in the Development of Molecularly Imprinted Polymer Sensors*, Arnold et al., Johns Hopkins APL Technical Digest, Vol. 20, No. 2 (1999) incorporated herein by this reference.

However, these molecular imprinted polymer designs suffer from the distinct disadvantage that they are designed to be specific to only one target analyte, are large, bulky, complex, delicate, and difficult to use.

SUMMARY OF THE INVENTION

It is therefore an object of this invention to provide a molecular recognition sensor system and method.

It is a further object of this invention to such a molecular recognition sensor system and method which can accurately detect an analyte.

It is a further object of this invention to provide such a molecular recognition sensor system and method which can accurately detect the concentration of an analyte.

It is a further object of this invention to provide such a molecular recognition sensor system and method which can detect a plurality of analytes.

It is a further object of this invention to provide such a molecular recognition sensor system and method which can detect a plurality of analyte concentrations.

It is a further object of this invention to provide such a molecular recognition sensor system which is compact, inexpensive and easy to use.

It is a further object of this invention to provide such a molecular recognition sensor system which is easily transportable.

It is a further object of this invention to provide such a molecular recognition sensor system which is simple in design.

It is a further object of this invention to provide such a molecular recognition sensor system and method which can eliminate the effect of interferents on the change of resistance of a resistive sensor when exposed to an analyte and interferents.

This invention results from the realization that a truly effective and robust molecular recognition sensor system can be achieved by the combination of first a resistive sensor including a semiconductive polymer film which swells when exposed to an analyte and interferents and second a molecular imprinted resistive sensor including a semiconductive polymer film imprinted with the analyte of interest and which swells when exposed to the interferents and then by detecting the change in resistance of the resistive sensor when exposed to the analyte and interferents and the change in resistance in the molecular imprinted resistive sensor when exposed to the analyte and interferents by subtracting the change in resistance of the molecular imprinted resistive sensor from the change in resistance of the resistive sensor thus eliminating the effect of the interferents on the change of resistance to the resistive sensor to thereby more accurately determine the presence and concentration of the analyte of interest.

This invention features a molecular recognition sensor system including a resistive sensor having a semiconductive polymer film which swells when exposed to an analyte and interferents and a molecular imprinted resistive sensor having a semiconductive polymer film imprinted with the analyte which thereby swells when exposed to interferents.

The system also includes a circuit connected to the resistive sensor and the molecular imprinted resistive sensor for detecting a change in the resistance of the resistive sensor when exposed to the analyte and the interferents, the change in the resistance of the molecular imprinted resistive sensor when exposed to the analyte and interferents, and for subtracting the change in resistance of the molecular imprinted resistive sensor from the change in resistance of the resistive sensor to reduce the effect of any interferents on the change in resistance of the resistive sensor thereby determining the presence and concentration of the analyte.

The circuit may be connected to an analog to digital converter which may be interfaced with a computer having software to read resistance.

The molecular recognition sensor system in accordance with this invention may also include a resistive sensor and molecular imprinted resistive sensor pair for each analyte of interest.

Ideally, the resistive sensor and the molecular resistive sensors include carbon or copper to make the polymere film conductive.

This invention also features a method of determining the presence and concentration of an analyte which includes the steps of forming a resistive sensor with a semiconductive polymer film which swells when exposed to the analyte and interferents, imprinting a semiconductor polymer film with an analyte forming a molecular imprinted resistive sensor which swells when exposed to interferents, detecting a change in the resistance of the resistive sensor when exposed to the analyte and the interferents and the change in the resistance of the molecular imprinted resistive sensor when exposed to the analyte and interferents, and subtracting the change in resistance of the molecular imprinted resistive sensor from the change in resistance of the resistive sensor to reduce the effect of any interferents effect on the change of resistance of the resistive sensor thereby determining the presence and concentration of the analyte.

BRIEF DESCRIPTION OF THE DRAWINGS

Other objects, features and advantages will occur to those skilled in the art from the following description of a preferred embodiment and the accompanying drawings, in which:

FIGS. 3A–3C are schematic side views showing a prior art polymer being imprinted with an analyte;

FIG. 4 is a typical prior art molecular imprinted polymer applied to a fiber-optic sensor in which luminescence is being used to detect an analyte;

DETAILED DESCRIPTION OF THE INVENTION

Figure 1:
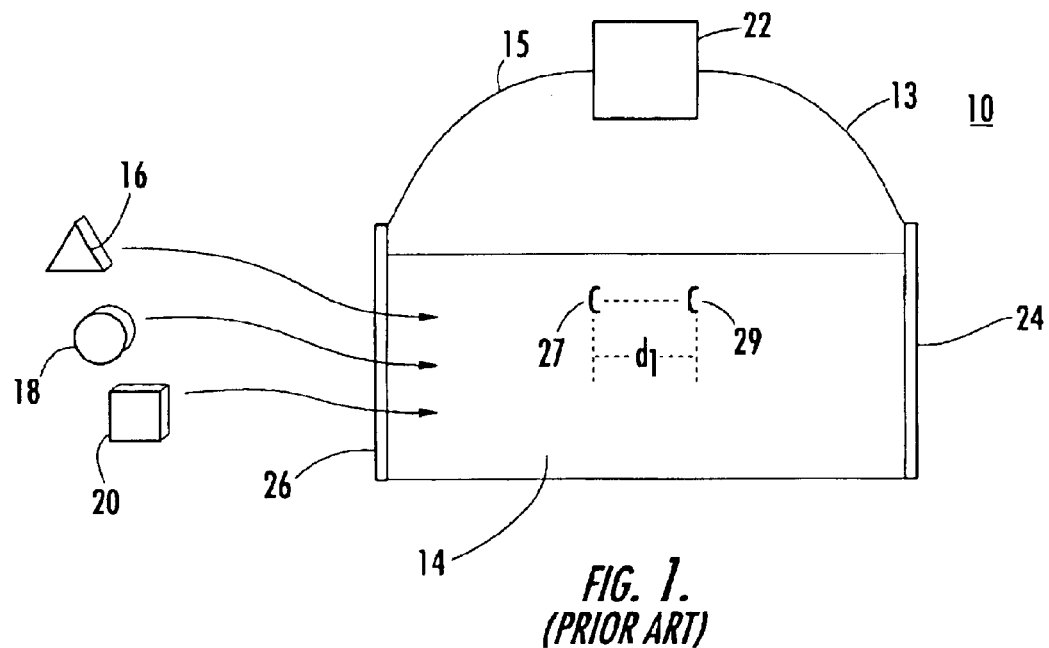
FIG. 1 is a schematic view of a prior art resistive sensor with a semiconductive polymer film being exposed to an analyte and interferents.
Figure 2:
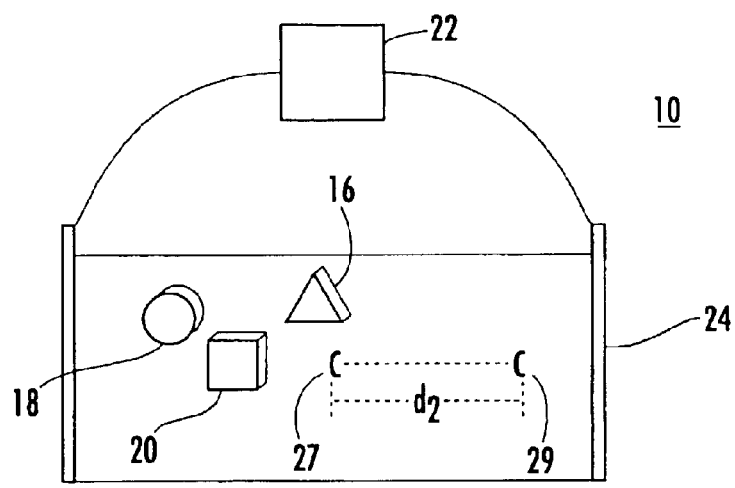
FIG. 2 is a schematic side view of a prior art resistive sensor showing the analyte and interferents absorbed by the semiconductive polymer film on the resistive sensor.

As explained in the Background of the Invention section above, typical prior art resistive sensor 10, FIG. 1 is used for chemical detection of analytes by measuring the change in resistance when analyte 16 and interferents 18 and 20 are absorbed by the semiconductive polymer film 14 on sensor 10. This technique relies on the microscopic swelling caused by analyte 16 and interferents 18 and 20 as they are absorbed by semiconductive polymer film 14. The resistive properties of semiconductive polymer film 14 increase because as analyte 16 and interferents 18 and 20 are absorbed by the film adjacent conductive molecules, such as carbon 27 and carbon 29 separated by distance $d_1$, are displaced further and further apart, as shown by distance $d_2$, FIG. 2. Accordingly, as the adjacent conductive molecules of carbon 27 and carbon 29 are displaced further and further apart the resistivity of semiconductive polymer film 14 increases. Resistance measuring device 22 is connected to contact pads 24 and 26 via wires 13 and 15 and measures the resistivity of resistive sensor 10 before and after it is exposed to analyte 16 and interferents 18 and 20. Resistive sensor 10 can accurately measure the resistive change due to the absorption of both analyte 16 and interferents 18 and 20 in semiconductive polymer film 14, but not the specific resistive change due to analyte 16.

However, this design suffers from the distinct disadvantages that semiconductive polymer film 14 will absorb a multitude of organic or bio-molecules, literally billions of possible compounds, which will mask the detection of analyte 16. Therefore, to be selective, prior art resistive sensor 10 must employ an array of chemical coatings on semiconductive polymer film 14 and rely on pattern recognition to detect an analyte of interest. As noted supra, prior art resistive sensor 10 is non-specific to an analyte of interest (i.e. measures the absorption of both analyte 16 and interferents 18 and 20), requires extensive data manipulation.

Other prior art methods use molecular imprinting of a polymer for specific detection of an analyte. As shown in FIG. 3A, typical prior art polymer 42 is exposed to analyte 44 which is absorbed by polymer 42, FIG. 3B. Polymer 14 is then cured and analyte 44 is removed by heating in the curing process, or by washing semiconductive polymer 42 with a suitable solvent such as water/methanol solution and rinsing with acid or similar solvents. See e.g. the Jenkens et al. and Arnold et al. papers cited in the Background of the Invention section above. The result is cavities 50 in polymer 42 in the exact shape and size of analyte 44, as shown in FIG. 3C. Polymer 42 may be applied to fiber-optic sensor 60, FIG. 4. Luminescence is excited using argon ion laser 62 with a holographic filter 64 and applied to fiber-optic sensor 60. The results can be analyzed using a monochromator and charge-coupled device camera 66 and computer 68. Similarly, the spectral properties of polymer 42 after analyte 44 is absorbed can be analyzed using fluorescence, phosphorescence, and UV, infrared, and visible light absorption.

However, as shown above, prior art molecular imprinted polymers suffer from the distinct disadvantage of being designed to be specific to only one target analyte. Further, these devices rely on complicated devices for measuring the spectral properties of analyte absorbed in the cavities of the polymer which are large, complex, delicate, difficult to use, and not easily transportable.

Figure 5:
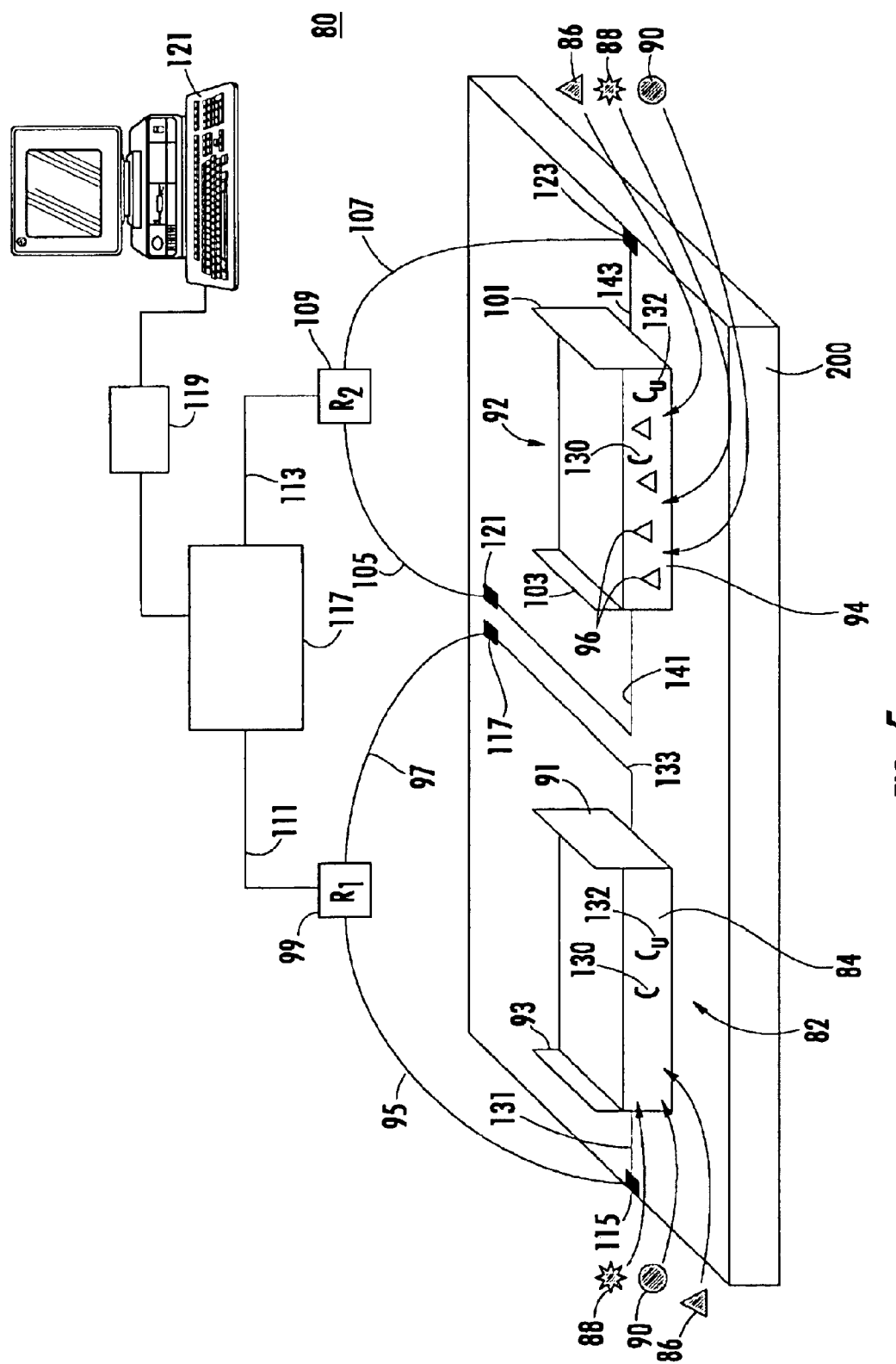
FIG. 5 is a schematic three-dimensional view of one embodiment of the molecular recognition sensor system in accordance with the subject invention.

In sharp contrast, molecular recognition sensor system 80, FIG. 5 of the subject invention includes resistive sensor 82 having semiconductive polymer film 84 which swells when exposed to analyte 86 and interferents 88 and 90 and molecular imprinted resistive sensor 92 including semiconductive polymer film 94 imprinted with analyte 86 which swells when exposed to interferents 88 and 90. Circuit 117 detects the change in resistance of resistive sensor 82 when exposed to analyte 86 and interferents 88 and 90 and the change in resistance of molecular imprinted resistive sensor 92 when exposed to analyte 86 and interferents 88 and 90. Circuit 117 then subtracts the change in resistance of molecular imprinted resistive sensor 92 from the change in resistance of the resistive sensor 82 to reduce the effect of interferents 88 and 90 on the change in resistance of resistive sensor 82 to accurately determine the presence and concentration of analyte 86.

Preferably, the polymer film of resistive sensor 84 and molecular imprinted resistive sensor 94, FIG. 5, includes carbon 130 or copper 132 to provide semiconductive properties to resistive sensor 82 and molecular imprinted resistive sensor 92.

Figure 6:
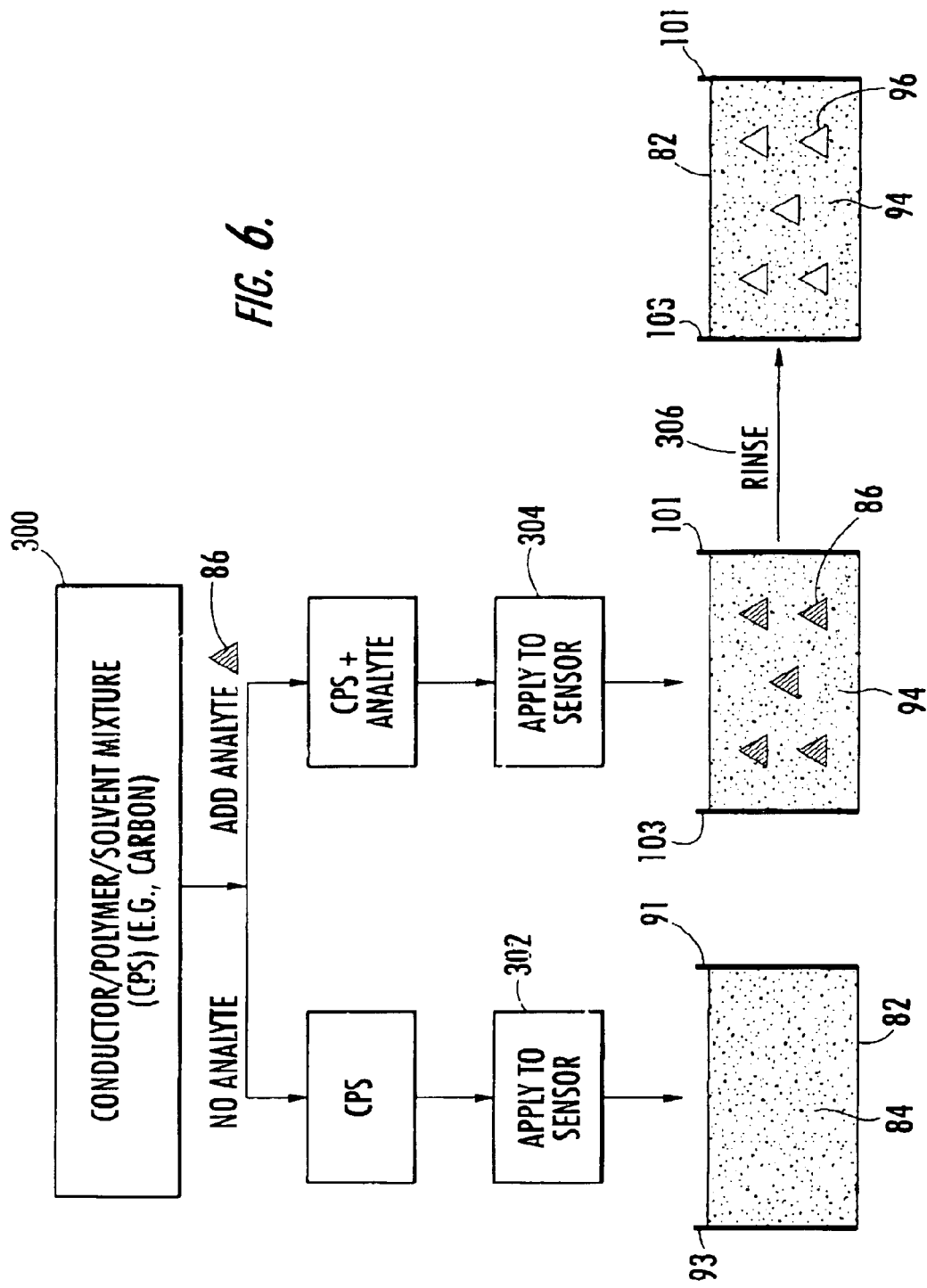
FIG. 6 is a flowchart of the fabrication of the resistive sensor and molecular imprinted resistive sensor in accordance with the subject invention.

Resistive sensor 82 is fabricated by applying conductive polymer solvent mixture 300, FIG. 6 to electrical contact pads 91 and 93, step 302, to form semiconductive polymer film 84 which swells when exposed to analyte 86 and interferents 88 and 90, which as noted supra will increase the resistivity of resistive sensor 92. See e.g. the Lewis patents cited in the Background of the Invention above. Contact pad 115, FIG. 5, is connected to contact pad 93 via lead 131 and contact pad 117 is connected to contact pad 91 via lead 133, all of which are mounted on non-conductive substrate 200. Contact pads 101,103,121, and 123 are typically made of copper or any suitable conducting material. The non-conductive substrate may be ceramic, plastic, or any suitable non-conductive material. Resistance measuring device 99 is connected to contact pads 115 and 117 via wires 95 and 97, respectively, and measures the change in resistance when resistive sensor 82 is exposed to analyte 86 and interferents 88 and 90. Resistance measuring device 99 may be an ohm meter, oscilloscope, or any other suitable device to measure resistance. Resistance measuring device 99 will measure the change in resistance when an analyte 86 and interferents 88 and 90 are absorbed by semiconductive polymer film 84 of resistive sensor 82.

Unique molecular imprinted resistive sensor 92 is fabricated by exposing conductive polymer solvent mixture 300, FIG. 6, to analyte 86 which impregnates conductive polymer solvent mixture 300. Conductive polymer solvent mixture 300 is applied to electrical contact pads 101 and 103, step 304, and cured by heating or similar processes to form semiconductive polymer film 94. Analyte 44 is removed from conductive polymer solvent mixture 300, step 306, by rinsing semiconductive polymer 94 with a suitable solvent such as water/methanol solution and then rinsing with an acid, such as acetic acid, or similar solvents/and or acids which will remove analyte 44. See e.g. the Jenkens et al and Arnold et al. papers cited in the Background of the Invention section above. The result is molecular imprinted resistive sensor 92 which includes semiconductive polymer film 94 with cavities 96 in the exact size and shape as analyte 86. Contact pad 121, FIG. 5, is connected to contact pad 103 via lead 141 and contact pad 123 is connected to contact pad 101 via lead 143. Contact pads 101, 103, 121 and 123, are typically made of copper or any suitable conducting material and mounted on non conductive substrate 200. Resistance measuring device 109 is connected to contact pads 121 and 123 via wires 105 and 107 respectively and measures the change in resistance when molecular imprinted resistive sensor 92 is exposed to analyte 86 and interferents 88 and 90. However, unlike resistive sensor 82, when molecular imprinted resistive sensor is exposed to analyte 86 and interferents 88 and 90 (at concentration of analyte 86 less than or equal to the concentration of cavities 96) semiconductive polymer film 94 will swell only due to interferents 88 and 90, not analyte 86, because analyte 86 will fill cavities 96 and not contribute to the swelling of semiconductive polymer film 94. Accordingly, molecular imprinted resistive sensor 92 will measure only the change in resistively due to interferents 88 and 90.

Electrical circuit 117 is connected to connected to resistance measuring devices 99 and 101 by leads 111 and 113 respectively. Typically, Electrical circuit 117 may be attached to A/D converter 119 which may be connected to computer 121 for analysis using an electronic spreadsheet, such as MICROSOFT EXCEL® or similar software. Circuit 117 detects the change in resistance of resistive sensor 82 when exposed to analyte 86 and interferents 88 and 90 and the change in resistance of molecular imprinted resistive sensor 92 when exposed to analyte 86 and interferents 88 and 90. Circuit 117 then subtracts the change in resistance of molecular imprinted resistive sensor 92 from the change in resistance of the resistive sensor 82 to reduce the effect of interferents 88 and 90 on the change in resistance of resistive sensor 82 and accurately determine the concentration of analyte 86. The result is a simple and accurate molecular recognition sensor system which can accurately determine the presence and concentration of an analyte without the need for complicated arrays of coatings on the sensor, pattern recognition, or lasers, filters, NMR spectrometry, or other complicated devices needed to measure the spectral properties of the absorbed analyte in a polymer. Moreover, the device is small, compact, durable and easily transportable.

Figure 7:
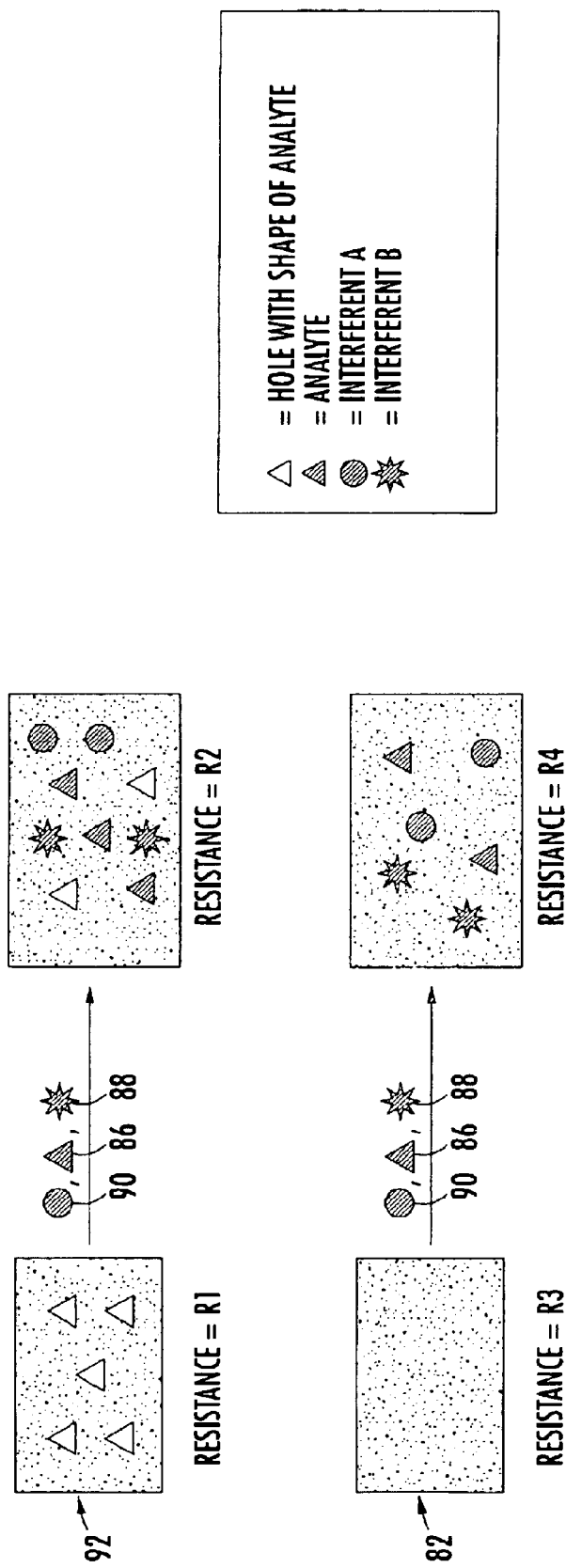
FIG. 7 is an enlarged view of the molecular imprinted resistive sensor and the resistive sensor shown in FIG. 5 being exposed to an analyte and interferents.

As shown in detail in FIG. 7, the resistivity of molecular imprinted resistive sensor 92 is measured before being exposed to analyte 86 and interferents 88 and 90, indicated as R1. Molecular imprinted resistive sensor 92 is then exposed to analyte 86 and interferents 88 and 90 and the resistively due to interferents 88 and 90 is measured, indicated as R2. Similarly, the resistivity of resistive sensor 82 is measured before being exposed to analyte 86 and interferents 88 and 90, indicated as R3. Resistive sensor 82 is exposed to analyte 86 and interferents 88 and 90 and the corresponding change of resistivity due to analyte 86 and interferents 88 and 90 is measured, indicated as R4. The net change in the resistively due only to analyte 86 is calculated as follows:

$$\frac{1}{R_2} = \frac{1}{R_1} + \frac{1}{R_*} + \frac{1}{R_\bullet}$$

$$R_2 = \frac{R_\bullet R_* + R_1 R_\bullet + R_1 R_*}{R_* R_\bullet R_1}$$

$$\frac{1}{R_4} = \frac{1}{R_3} + \frac{1}{R_*} + \frac{1}{R_\bullet} + \frac{1}{R_\Delta}$$

$$R_4 = \frac{R_* R_\bullet R_\Delta + R_3 R_* R_\Delta + R_3 R_\bullet R_*}{R_3 R_* R_\bullet R_\Delta}$$

$$\frac{1}{R_4} - \frac{1}{R_2} = \frac{1}{R_3} + \frac{1}{R_\Delta} - \frac{1}{R_1}$$

$$\frac{1}{R_\Delta} = \frac{1}{R_4} - \frac{1}{R_2} - \frac{1}{R_3} + \frac{1}{R_1}$$

$$R_\Delta = \frac{R_2 R_3 R_4 - R_1 R_3 R_4 - R_1 R_2 R_4 + R_1 R_2 R_3}{R_1 R_2 R_3 R_4}$$

Figure 8:
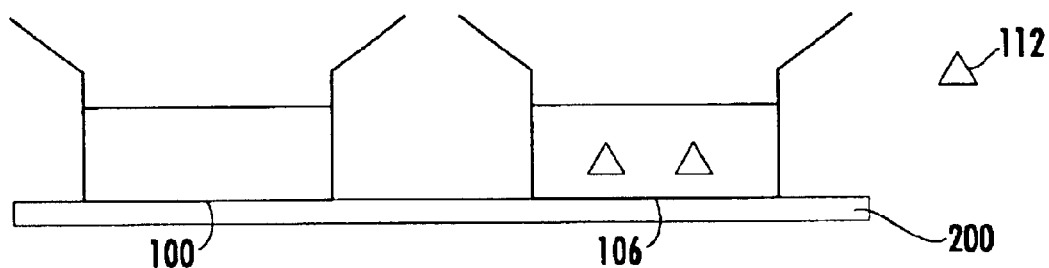
FIG. 8 is a schematic side view showing a resistive sensor and molecular imprinted resistive sensor pair for each analyte of interest in accordance with the subject invention.
Figure 8:
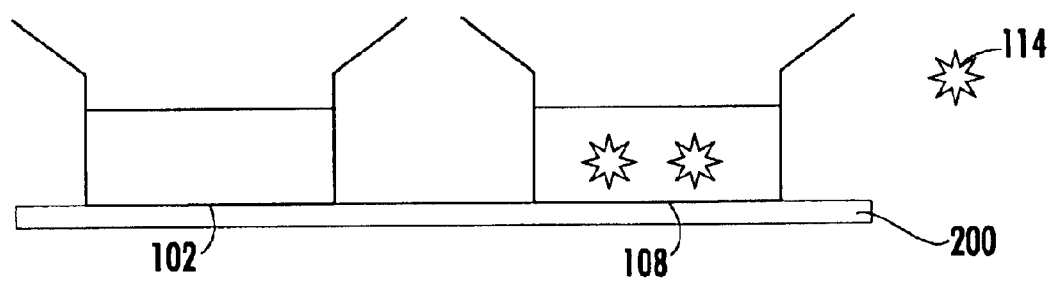
Figure 8:
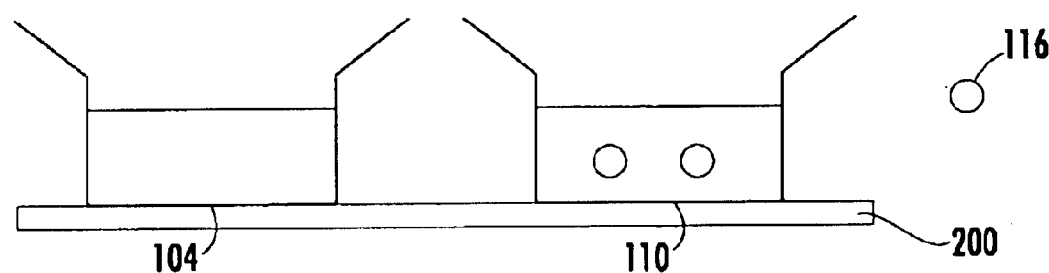

In one preferred embodiment in accordance with the subject invention, molecular recognition system 80 includes a resistive sensor and molecular imprinted resistive sensor pair for each analyte of interest. For example, as shown in FIG. 8, resistive sensors 100, 102 and 104 are electrically connected in parallel and paired with molecular imprinted resistive sensors 106, 108 and 110 respectively, which are mounted on non-conductive substrate 200. Specifically, resistive sensor 100 is paired with molecular imprinted resistive sensor 106 for detecting analyte 112, resistive sensor 102 is paired with molecular imprinted resistive sensor 108 for detecting analyte 114, and resistive sensor 104 is paired with molecular imprinted resistive sensor 110 for detecting analyte 116. The result is that molecular recognition sensor system 80 of the subject invention can detect a plurality of analytes and/or analytes concentrations in a simple, compact, easy to use design.

Figure 9:
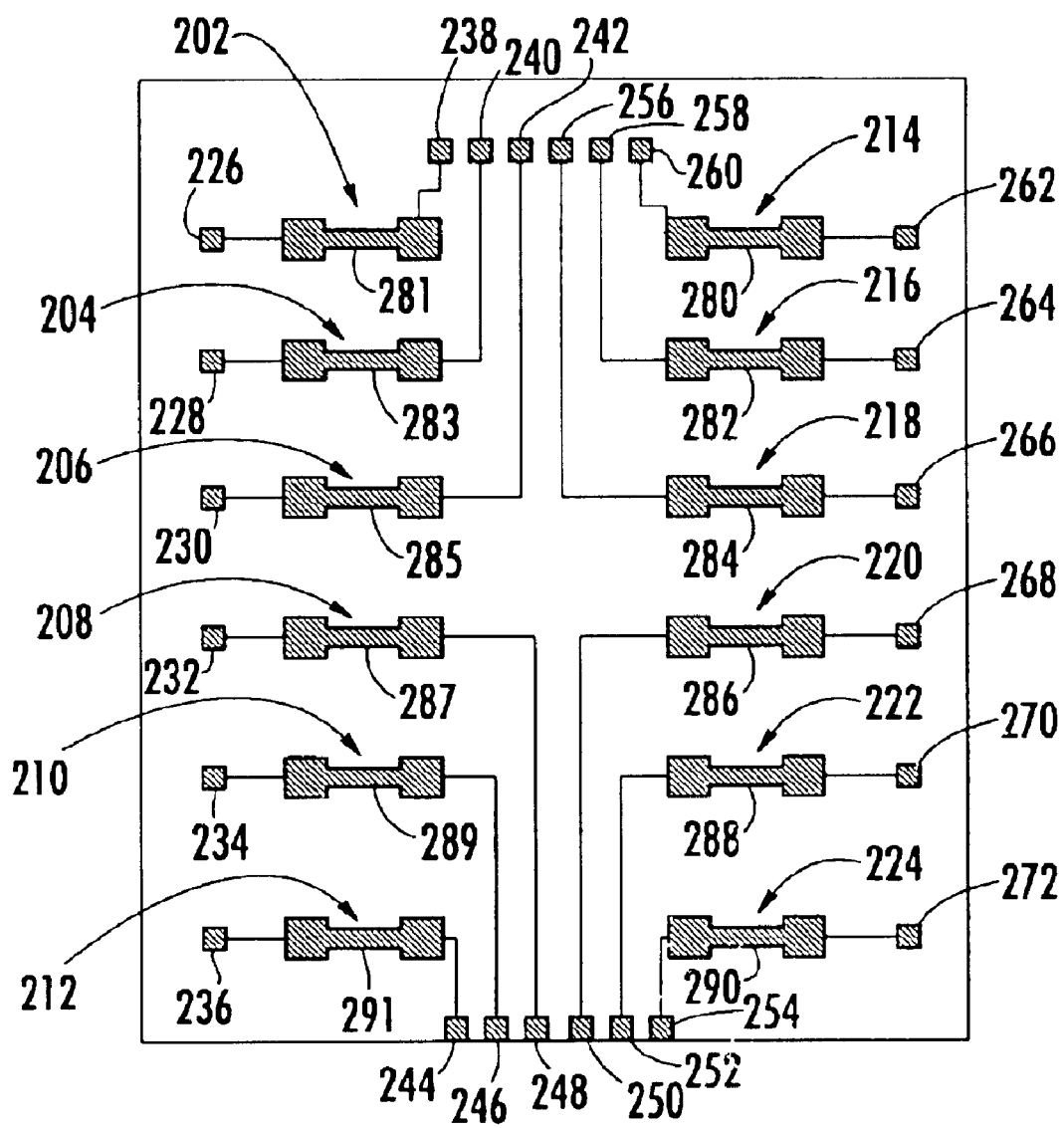
FIG. 9 is a schematic top view showing of the molecular recognition sensor system with an array of resistive sensors and molecular imprinted resistive sensors in accordance with the subject invention.

In a preferred embodiment of the subject invention, molecular recognition system 80, FIG. 9 includes a plurality of resistive sensors 202, 204, 206, 208, 210 and 212 electrically connected in parallel and paired with a plurality of molecularly imprinted resistive sensor 214, 216, 218, 220, 222 and 224, respectively. Contact pads 226–248 of resistive sensors 202–212 provide a connection a resistance measuring device. Similarly, contact pads 250–272 of molecular imprinted resistive sensors 214–224 provide a connection to a resistance measuring device. Molecularly imprinted resistive sensors 214–224 include semiconductive polymer film 280, 282, 284, 286, 288, and 290, respectively, having a range of cavities from 0 to 5% to accommodate for a vast array of analyte concentration. The result is a molecular recognition sensor system which can tolerate a wide range of analyte concentrations before the cavities of the molecular imprinted sensor are filled.

Figure 10:
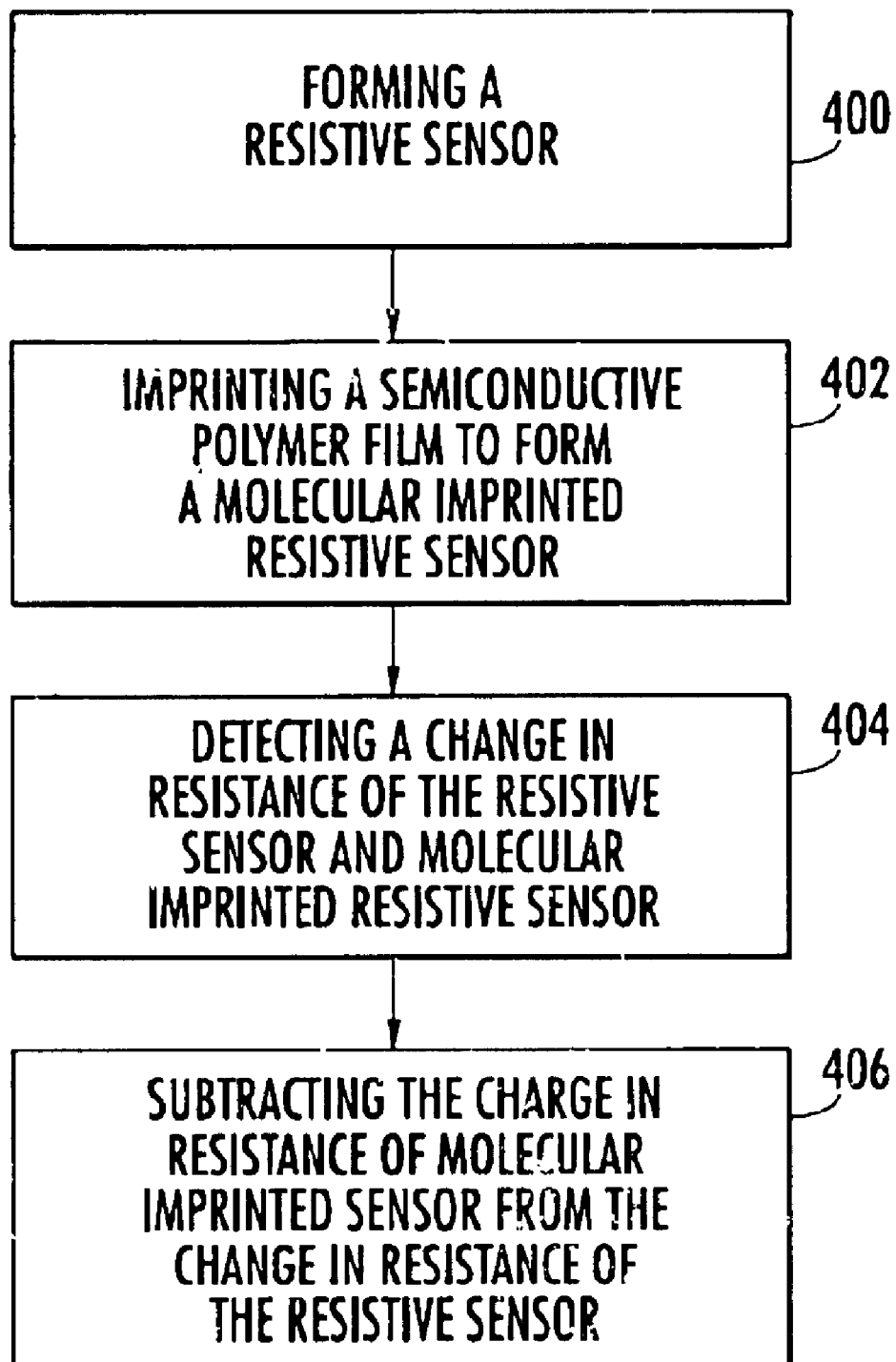
FIG. 10 is a flow chart of the method of determining the presence and concentration of an analyte.

This invention also features a method of detecting the concentration of an analyte, FIG. 10, which includes the steps of: forming a resistive sensor which swells when exposed to an analyte and interferents, step 400, imprinting a semiconductive polymer film with analyte to form a molecular imprinted resistive sensor which swells when exposed to interferents, step 402, detecting the change in the resistance of the resistive sensor when exposed analyte and interferents and the change in resistance of the molecular imprinted resistive sensor when exposed to the analyte and interferents, step 404, and subtracting the change in resistance of the molecular imprinted resistive sensor from the change in resistance of the resistive sensor to reduce the effect of interferents on the change the resistance of resistive sensor thereby determining the concentration of the analyte, step 406.

The unique molecular recognition sensor system of the subject invention includes molecular imprinted resistive sensor 92 which allows the effects of the interferents to be subtracted from the resistive sensor. The result is a molecular recognition sensor system and method which is simple in design yet can accurately detect a plurality of analytes and/or analyte concentrations regardless of the concentration of interferents. The system is compact, durable, inexpensive, and easily transportable. Moreover, the need for large complicated lasers, filters, NMR spectrometry, and other complicated devices needed to measure the spectral properties of an absorbed analyte in a molecularly imprinted polymer are eliminated.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A molecular recognition sensor system comprising:
   a resistive sensor including a semiconductive polymer film which swells when exposed to an analyte and interferents;
   a molecular imprinted resistive sensor including a semiconductive polymer film imprinted with the analyte to produce cavities therein, in which the film thereby swells when exposed to interferents but not analytes when said analytes are at a concentration less than or about equal to a concentration of the cavities; and
   a circuit connected to the resistive sensor and the molecular imprinted resistive sensor for detecting a change in the resistance of the resistive sensor when exposed to the analyte and the interferents, the change in the resistance of the molecular imprinted resistive sensor when exposed to the analyte and interferents, and for subtracting the change in resistance of the molecular imprinted resistive sensor from the change in resistance of the resistive sensor to reduce the effect of any interferents on the change in resistance of the resistive sensor thereby determining the presence and concentration of the analyte.

2. The sensor system of claim 1 further including a resistive sensor and molecular imprinted resistive sensor pair for each analyte of interest.

3. The sensor system of claim 1 in which the polymer film of the resistive sensor includes carbon.

4. The sensor system of claim 1 in which the polymer film of the molecular imprinted resistive sensor includes carbon.

5. The sensor system of claim 1 in which the polymer film of the resistive sensor includes copper.

6. The sensor system of claim 1 in which the polymer film of the molecular imprinted resistive sensor includes copper.

7. The sensor system of claim 1 in which the circuit is connected to an analog to digital converter.

8. The sensor system of claim 7 in which the analog to digital converter is interfaced with a computer having software to read resistance.

9. A method of determining the presence and concentration of an analyte, the method comprising:
   forming a resistive sensor with a semiconductive polymer film which swells when exposed to the analyte and interferents;
   imprinting a semiconductor polymer film with an analyte forming a molecular imprinted resistive sensor having cavities therein, in which the resistive sensor swells when exposed to interferents, but not to analytes when said analytes are at a concentration less than or about equal to a concentration of the cavities;
   detecting a change in the resistance of the resistive sensor when exposed to the analyte and the interferents and the change in the resistance of the molecular imprinted resistive sensor when exposed to the analyte and interferents; and
   subtracting the change in resistance of the molecular imprinted resistive sensor from the change in resistance of the resistive sensor to reduce the effect of any interferents on the change of resistance of the resistive sensor thereby determining the presence and concentration of the analyte.

10. The method of claim 9 in which the polymer film of the resistive sensor includes carbon.

11. The method of claim 9 in which the polymer film of the molecular imprinted resistive sensor includes carbon.

12. The method of claim 9 in which the polymer film of the resistive sensor includes copper.

13. The method of claim 9 in which the polymer film of the molecular imprinted resistive sensor includes copper.

14. A molecular recognition sensor system comprising:
   a resistive sensor including a semiconductive polymer him including copper which swells when exposed to an analyte and interferents;

a molecular imprinted resistive sensor including a semiconductive polymer film imprinted with the analyte which thereby swells when exposed to interferents; and a circuit connected to the resistive sensor and the molecular imprinted resistive sensor for detecting a change in the resistance of the resistive sensor when exposed to the analyte and the interferents, the change in the resistance of the molecular imprinted resistive sensor when exposed to the analyte and interferents, and for subtracting the change in resistance of the molecular imprinted resistive sensor from the change in resistance of the resistive sensor to reduce the effect of any interferents on the change in resistance of the resistive sensor thereby determining the presence and concentration of the analyte.

15. The sensor system of claim 14 in which the polymer film of the molecular imprinted resistive sensor includes copper.

16. A method of determining the presence and concentration of an analyte, the method comprising:

forming a resistive sensor with a semiconductive polymer film including copper which swells when exposed to the analyte and interferents;

imprinting a semiconductor polymer film with an analyte forming a molecular imprinted resistive sensor which swells when exposed to interferents;

detecting a change in the resistance of the resistive sensor when exposed to the analyte and the interferents and the change in the resistance of the molecular imprinted resistive sensor when exposed to the analyte and interferents; and subtracting the change in resistance of the molecular imprinted resistive sensor from the change in resistance of the resistive sensor to reduce the effect of any interferents on the change of resistance of the resistive sensor thereby determining the presence and concentration of the analyte.

17. The method of claim 16 in which the polymer film of the molecular imprinted resistive sensor includes copper.

* * * * *